(12) United States Patent
Ibuki et al.

(10) Patent No.: US 11,559,003 B2
(45) Date of Patent: Jan. 24, 2023

(54) YIELD CALCULATION SYSTEM, YIELD MAP GENERATION SYSTEM, METHOD OF CALCULATING YIELD FOR BALER, AND COMPUTER READABLE STORAGE MEDIUM

(71) Applicant: Kubota Corporation, Osaka (JP)

(72) Inventors: Takeru Ibuki, Amagazaki (JP);
Hirokazu Sasamoto, Amagazaki (JP);
Sakura Sasakura, Amagazaki (JP);
Yasuhiro Nishida, Sakai (JP)

(73) Assignee: KUBOTA CORPORATION, Osaka (JP)

( * ) Notice: Subject to any disclaimer, the term of this patent is extended or adjusted under 35 U.S.C. 154(b) by 135 days.

(21) Appl. No.: 17/088,578

(22) Filed: Nov. 4, 2020

(65) Prior Publication Data

US 2021/0137015 A1    May 13, 2021

(30) Foreign Application Priority Data

Nov. 7, 2019   (JP) .............................. JP2019-202435

(51) Int. Cl.
*A01F 15/08* (2006.01)
*G01N 33/00* (2006.01)
*A01F 15/07* (2006.01)

(52) U.S. Cl.
CPC ......... *A01F 15/08* (2013.01); *G01N 33/0098* (2013.01); *A01F 15/07* (2013.01)

(58) Field of Classification Search
CPC .. A01F 15/08; A01F 15/07; A01F 2015/0891; A01F 15/0825; G01N 33/0098; A01B 79/005

See application file for complete search history.

(56) References Cited

U.S. PATENT DOCUMENTS

| 10,289,696 B2 | 5/2019 | Derscheid |
| 2004/0002368 A1* | 1/2004 | Shinners .............. A01D 43/085 460/4 |

(Continued)

FOREIGN PATENT DOCUMENTS

| AU | 2010101429 | 2/2011 |
| EP | 3254554 | 12/2017 |

(Continued)

OTHER PUBLICATIONS

Extended European Search Report for corresponding EP Application No. 20203872.5-1004, dated Mar. 31, 2021.

(Continued)

*Primary Examiner* — Tarun Sinha
*Assistant Examiner* — Yossef Korang-Beheshti
(74) *Attorney, Agent, or Firm* — Mori & Ward, LLP

(57) ABSTRACT

A yield calculation system comprises a position sensor configured to detect a position. A baler comprises a bale chamber in which crop material is to be formed into a bale, a volume measurement sensor provided in the bale chamber and configured to measure a volume of the bale in the bale chamber, the volume corresponding to the position detected by the position sensor, and a moisture measurement sensor provided in the bale chamber and configured to measure a moisture amount in the bale, the moisture amount corresponding to the position detected by the position sensor. Circuitry is configured to calculate, based on the volume of the bale and the moisture amount corresponding to the position, a yield corresponding to the position by excluding the moisture amount from an amount of the bale.

17 Claims, 8 Drawing Sheets

(56) References Cited

U.S. PATENT DOCUMENTS

| | | | | |
|---|---|---|---|---|
| 2009/0217827 | A1* | 9/2009 | Duenwald | A01F 15/0833 100/88 |
| 2013/0152534 | A1* | 6/2013 | Clark | A01D 41/127 56/10.2 B |
| 2017/0354092 | A1* | 12/2017 | Lang | A01F 15/08 |
| 2018/0121467 | A1* | 5/2018 | Derscheid | G05B 15/02 |
| 2019/0265043 | A1 | 8/2019 | Lang et al. | |
| 2020/0319649 | A1 | 10/2020 | Unesaki et al. | |

FOREIGN PATENT DOCUMENTS

| | | |
|---|---|---|
| JP | 2003-061454 | 3/2003 |
| JP | 2006-254758 | 9/2006 |
| JP | 2007-135502 | 6/2007 |
| JP | 2007-295932 | 11/2007 |
| JP | 2016-202117 | 12/2016 |
| JP | 2018-099053 | 6/2018 |
| JP | 2018-185594 | 11/2018 |
| JP | 2019-118273 | 7/2019 |
| JP | 2019-126268 | 8/2019 |

OTHER PUBLICATIONS

Japanese Decision of a Patent Grant for corresponding JP Application No. 2019-202435, dated Sep. 6, 2022 (w/ machine translation).
Japanese Office Action for corresponding JP Application No. 2019-202435, dated Aug. 9, 2022 (w/ machine translation).

\* cited by examiner

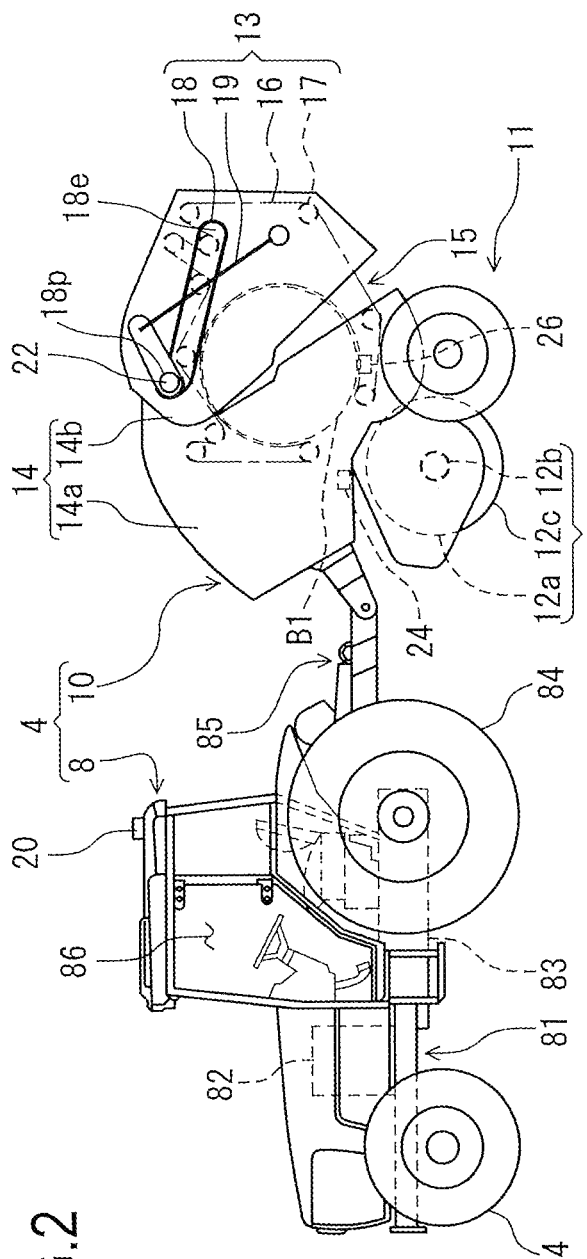
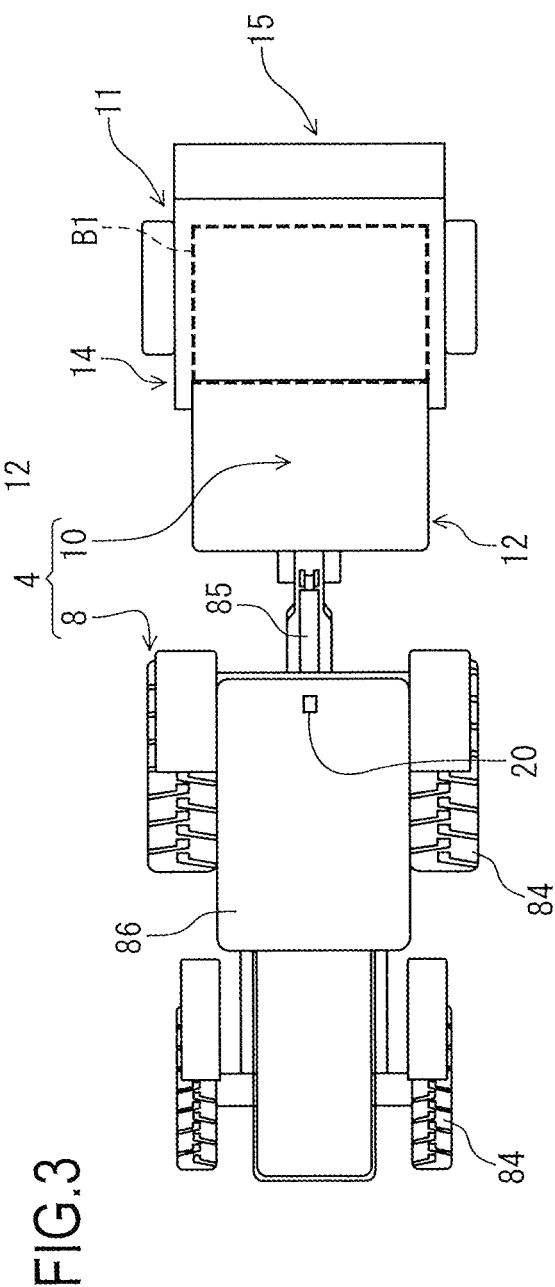
FIG.2
FIG.3

YIELD CALCULATION SYSTEM, YIELD MAP GENERATION SYSTEM, METHOD OF CALCULATING YIELD FOR BALER, AND COMPUTER READABLE STORAGE MEDIUM

CROSS-REFERENCE TO RELATED APPLICATIONS

The present application claims priority under 35 U.S.C. § 119 to Japanese Patent Application No. 2019-202435, filed Nov. 7, 2019. The contents of this application are incorporated herein by reference in their entirety.

BACKGROUND OF THE INVENTION

Field of the Invention

The present invention relates to a yield calculation system, a yield map generation system, a method of calculating a yield for a baler, and a computer readable storage medium.

Discussion of the Background

U.S. Pat. No. 10,289,696 discloses a method of generating a yield map based on a weight of a bale and a traveling route, the bale having been formed from a crop material that has been harvested by a baler, the baler having travelled to create the bale along the travelling route.

An objective of a technology disclosed in the present application is to provide: a yield calculation system for calculating a yield of the crop material which is less subject to a climate; a yield map generation system for calculating a yield of the crop material which is less subject to a climate; a method of calculating a yield which is less subject to a climate; a computer program comprising instructions which, when executed by a computer, cause the computer to carry out the method of calculating the yield; and a computer readable storage medium comprising instructions which, when executed by a computer, cause the computer to carry out the method of calculating the yield.

SUMMARY OF THE INVENTION

According to one aspect of the present disclosure, a yield calculation system includes a position sensor configured to detect a position, a baler, and circuitry. The baler includes a bale chamber, a volume measurement sensor, and a moisture measurement sensor. The crop material is to be formed into a bale in the bale chamber. The volume measurement sensor is provided in the bale chamber. The volume measurement sensor is configured to measure a volume of the bale in the bale chamber, the volume corresponding to the position detected by the position sensor. The moisture measurement sensor is provided in the bale chamber. The moisture measurement sensor is configured to measure a moisture amount in the bale, the moisture amount corresponding to the position detected by the position sensor. The circuitry is configured to calculate, based on the volume of the bale and the moisture amount corresponding to the position, a yield corresponding to the position by excluding the moisture amount from an amount of the bale.

According to another aspect of the present disclosure, a method of calculating a yield for a baler includes: obtaining a position at which the baler harvests a crop material; obtaining a volume of a bale into which the crop material is formed in a bale chamber of the baler, the volume of the bale corresponding to the position; obtaining a moisture amount in the bale, the moisture amount corresponding to the position; and calculating, based on the volume of the bale and the moisture amount corresponding to the position, the yield corresponding to the position by excluding the moisture amount from an amount of the bale.

According to further aspect of the present disclosure, a non-transitory computer-readable storage medium storing a program for causing a computer to perform a method of calculating a yield for a baler. The method includes: obtaining a position at which the baler harvests a crop material; obtaining a volume of a bale into which the crop material is formed in a bale chamber of the baler, the volume of the bale corresponding to the position; obtaining a moisture amount in the bale, the moisture amount corresponding to the position; and calculating, based on the volume of the bale and the moisture amount corresponding to the position, the yield corresponding to the position by excluding the moisture amount from an amount of the bale.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

FIG. 2 is a side view of a harvester.

FIG. 3 is a plan view of the harvester.

DESCRIPTION OF THE EMBODIMENTS

Figure 1:
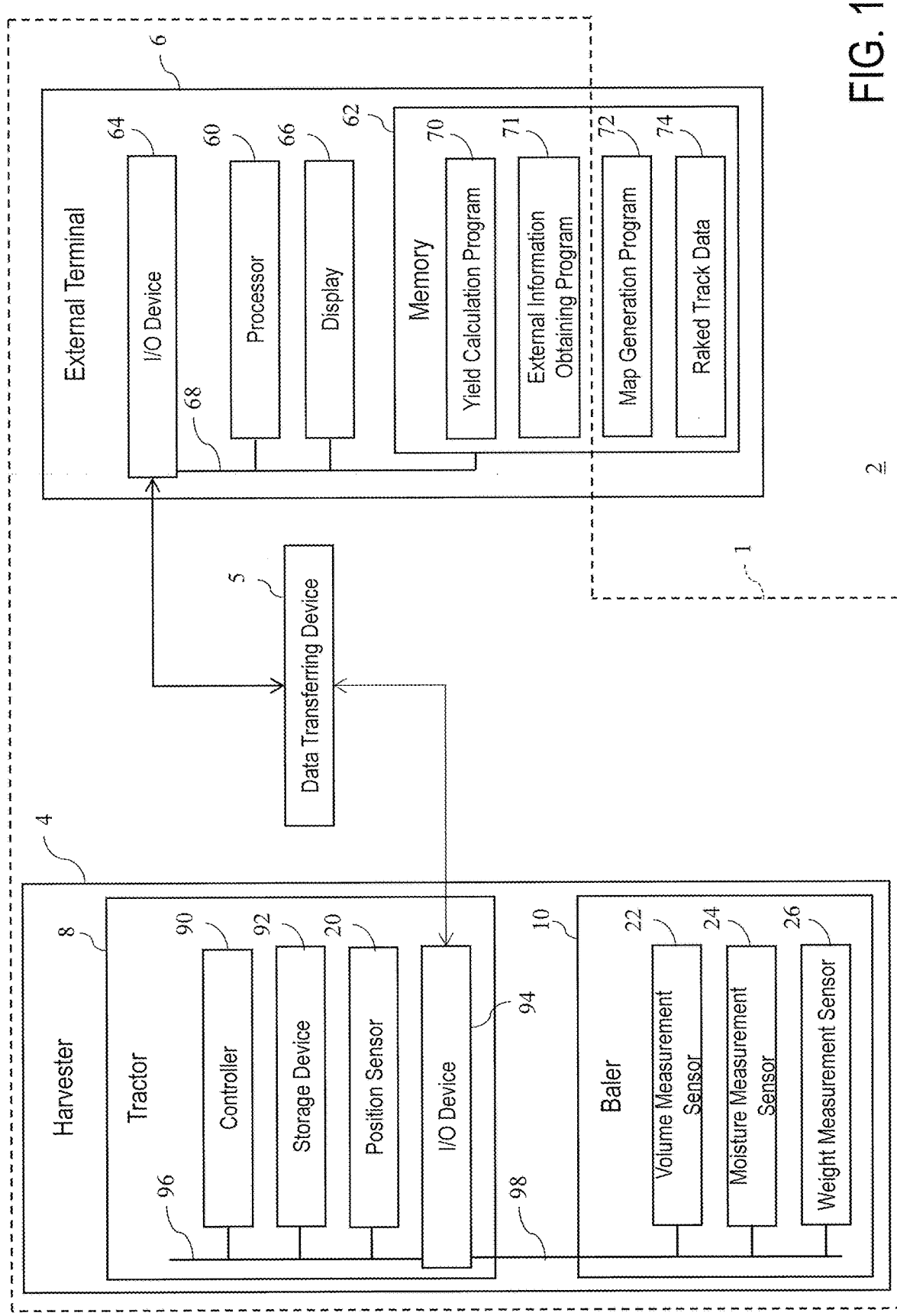
FIG. 1 is an overall diagram illustrating a yield map generation system including a yield calculation system in an embodiment.

The embodiments will now be described with reference to the accompanying drawings, wherein like reference numerals designate corresponding or identical elements throughout the various drawings.

FIG. 1 is a yield map generation system 2 including a yield calculation system 1 in an embodiment. The yield map generation system 2 includes a harvester 4 to form and discharge a crop material of a field and an external terminal 6 to create a yield map in which a yield of the crop material harvested by the harvester 4 is shown in each of the regions of the field. The yield calculation system 1 is a system to calculate the yield in the yield map generation system 2. The harvester 4 may include all or a part of functions of the external terminal 6.

FIGS. 2 and 3 are a side view and a plan view of the harvester 4, respectively. The harvester 4 is configured to harvest a crop material. The crop material is generally grass. The harvester 4 includes a tractor 8 and a baler 10. The tractor 8 is configured to move the baler 10. The tractor 8 includes a vehicle body 81, a prime mover 82, and a transmission 83. The vehicle body 81 is provided with a traveling device 84. The traveling device 84 has front wheels and rear wheels. The traveling device 84 may be a crawler device. In this embodiment, the prime mover 82 is a diesel engine. However, the prime mover 82 can be an electric motor, or the like. The transmission 83 can switch propulsive force of the traveling device 84 and can switch the traveling device 84 between forward and reverse movements. In addition, a connecting unit 85 including a three-point link mechanism or the like is provided in a rear portion of the vehicle body 81. The baler 10 is detachable from the connecting unit 85. Connecting the baler 10 to the connecting unit 85 allows the vehicle body 81 to pull the baler 10. Also, the tractor 8 includes a power take-off (PTO) shaft driven by the power of the prime mover 82 or the like and can transmit the power of the PTO shaft to a work device. Also, the tractor 8 includes a cabin 86 including a driver's seat therein.

As illustrated in FIGS. 1 to 3, the yield calculation system 1 includes a position sensor 20. The position sensor 20 is, for example, a Global Positioning System (GPS) module. That is, the position sensor 20 is configured to receive a signal transmitted from a positioning satellite (position of the positioning satellite, transmission time, correction information, and the like; hereinafter, all of them are collectively referred to as positioning signals) and to detect the position (for example, latitude and longitude) based on the received signal. Alternatively, the position sensor 20 may be an inertial navigation system or a sensor using another position measurement system such as a position measurement system using cellular phone base stations. The position sensor 20 is provided on at least one of the baler 10 and the tractor 8. In this embodiment, the position sensor 20 is installed on a top plate of the cabin 86 of the tractor 8. Note that although the position sensor 20 is installed on the top plate of the cabin 86, the position sensor 20 may be installed on another place of the tractor 8. Alternatively, the position sensor 20 may be installed in the baler 10. Since the position sensor 20 is provided in the harvester 4, it is possible to detect the positions (machine positions at the time of forming work) at the time of harvesting work (at the time of traveling).

The baler 10 is configured to harvest a crop material in the field and to form harvested crop material into a predetermined shape. The predetermined shape includes a roll shape and a rectangular shape (cube shape). In this embodiment, the baler 10 is, for example, a round baler to form the crop material into a roll shape. However, the baler 10 can be a square baler to form the crop material into a rectangular shape.

As illustrated in FIGS. 2 and 3, the baler 10 includes a vehicle body 11 and a gathering unit 12. The vehicle body 11 is movable. The gathering unit 12 is supported by the vehicle body 11. The crop material is to be taken into the baler via the gathering unit 12. The gathering unit 12 is configured to gather in mowed crop material in the field from a front side (a side of the tractor 8), and includes, for example, a casing 12a whose front side is open. In addition, the gathering unit 12 includes a rotating shaft 12b supported by the casing 12a or the like, and a guide tool 12c fixed to the rotating shaft 12b. Therefore, rotating the rotating shaft 12b allows the guide tool 12c to gather in the crop material in the field into the casing 12a. Note that the gathering unit 12 of FIG. 2 is one example and is not limited to the above-described gathering unit 12.

The baler 10 includes a bale chamber 14 and a discharge unit 15. The bale chamber 14 is configured to accommodate the crop material taken in by the gathering unit 12. In the bale chamber 14, the crop material is to be formed into a bale B1. The discharge unit 15 is configured to discharge the crop material to the field. The bale chamber 14 includes a first case body 14a fixed to the vehicle body 11 and a second case body 14b that is vertically swingable with respect to the first case body 14a. The first case body 14a communicates with the gathering unit 12, and the crop material taken in by the gathering unit 12 enters the first case body 14a. When the second case body 14b is close to the first case body 14a (when the second case body 14b is swung downward), the bale chamber 14 accommodates the crop material. Meanwhile, when the second case body 14b is separated from the first case body 14a (when the second case body 14b is swung upward), the crop material is discharged from the bale chamber 14. That is, the discharge unit 15 is formed between the first case body 14a and the second case body 14b when the second case body 14b is swung upward with respect to the first case body 14a. Note that the bale chamber 14 and the discharge unit 15 of FIGS. 2 and 3 are one example and are not limited to the aforementioned bale chamber 14 and the discharge unit 15. Note that for convenience of description, a state where the second case body 14b is swung downward with respect to the first case body 14a may be referred to as a closed state (gate closed state), whereas a state where the second case body 14b is swung upward with respect to the first case body 14a may be referred to as an open state (gate open state).

The baler 10 includes a forming unit 13. The forming unit 13 is configured to form the crop material taken in by the gathering unit 12. The forming unit 13 is provided in the first case body 14a and the second case body 14b. The forming unit 13 is, for example, configured to form a roll-shaped bale B1. The forming unit 13 includes a belt 16 for fixing an external shape of the bale B1, a plurality of rollers 17 to support the belt 16, and a belt tensioning device 18 to maintain a tension of the belt 17. The belt tensioning device 18 is configured to rotate around a pivot 18p in accordance with a diameter of the bale B1. The forming unit 13 further includes an elastic member 19 to pull the belt tensioning device 18 such that a distal portion 18e of the belt tensioning device 18 with respect to the pivot 18p moves toward a center of the bale chamber 14. Note that the forming unit 13 may be a chain device configured to form the crop material into a roll with a chain, or a device of any other type. Therefore, the forming unit 13 can form the crop material taken in the bale chamber 14 into the bale B1 that has a predetermined shape.

As illustrated in FIGS. 1 and 2, the baler 10 further includes a volume measurement sensor 22, a moisture measurement sensor 24, and a weight measurement sensor 26. The volume measurement sensor 22, the moisture measurement sensor 24, and the weight measurement sensor 26 are provided in the bale chamber 14. Specifically, the moisture measurement sensor 24 is preferably provided adjacent to the gathering unit 12. The weight measurement sensor 26 is preferably provided on the forming unit 13 or discharge unit 15.

The volume measurement sensor 22 is configured to measure a volume of the bale B1 in the bale chamber 14, the volume corresponding to the position detected by the position sensor 20. For example, in a case where the bale B1 has a roll shape, the volume measurement sensor 22 is configured to measure a diameter of the bale B1. This is because a height of the roll shape is determined by a width of the bale chamber 14. The volume measurement sensor 22 is, for example, a potentiometer to detect a rotation angle of the pivot 18*p*. Since there is a predetermined correspondence between a rotation angle of the pivot 18*p* and a diameter of the bale B1, it is possible to obtain the diameter of the bale B1 from the rotation angle of the pivot 18*p*. The volume measurement sensor 22 is configured to output the volume of the bale B1 to which a time of the position sensor 20 is attached. The outputted volume of the bale B1 corresponds to the position of the harvester 4 at the time attached to the outputted volume of the bale B1. The volume measurement sensor 22 can measure an increment of the volume of the bale B1 in a predetermined cycle constituted by at least one of a predetermined time and an amount of change of the position. The increment of the volume in the predetermined time is, for example, an increment of the volume in a sampling interval. The increment of the volume in the amount of change of the position is, for example, an increment of the volume in a period during which the harvester 4 moves by the amount of change. When the harvester 4 travels in a constant speed, the predetermined cycle is constituted by the predetermined time as well as the amount of change of the position.

The moisture measurement sensor 24 is configured to measure a moisture amount in the bale B1, the moisture amount corresponding to the position detected by the position sensor 20. More specifically, the moisture measurement sensor 24 is configured to measure a moisture amount in the increment of the volume of the bale B1 in the predetermined cycle. The moisture measurement sensor 24 is, for example, a spectroscopic sensor. The moisture measurement sensor 24 is configured to irradiate the crop material with a light having a predetermined frequency, to receive a reflected light from internal parts of the crop material, and to detect the moisture amount in the crop material by measuring an amount of absorption of the light at the predetermined frequency by the moisture in the crop material. The moisture measurement sensor 24 is configured to output a moisture weight ratio indicating a ratio of a moisture weight in a sample irradiated by the light to a weight of the sample. That is, the moisture amount is represented by the moisture weight ratio. The moisture measurement sensor 24 is configured to output the moisture weight ratio to which a time of the position sensor 20 is attached. The outputted moisture weight ratio corresponds to the position of the harvester 4 at the time attached to the outputted moisture weight ratio. Accordingly, since the moisture weight ratio can be correlated with the increment of the volume of the bale B1, the moisture amount in the crop material can be represented by the moisture weight ratio indicating a ratio of a moisture weight in the increment to the weight of the increment.

The weight measurement sensor 26 is configured to measure a reference bale weight indicating a weight of a reference volume of the bale B1, when the volume of the bale B1 amounts to the reference volume. The reference volume is, for example, a volume of a completed bale that is formed just before discharged from the bale chamber 14. The weight measurement sensor 26 is, for example, a load cell to detect a weight. Note that the weight measurement sensor 26 may be another weight sensor. The reference bale weight is measured when the harvester 4 is stopped before the completed bale is discharged from the bale chamber 14. In a case where the weight measurement sensor 26 is resistant to vibration caused by the movement of the harvester 4 and vibration caused by rotation of the bale B1, the weight of the bale B1 may be measured during the movement of the harvester 4. In this case, the reference volume may not be the volume of the completed bale. The weight measurement sensor 26 is configured to output the reference bale weight to which a time of the position sensor 20 is attached. The outputted reference bale weight corresponds to the position of the harvester 4 at the time attached to the outputted reference bale weight.

As shown in FIG. 1, the volume measurement sensor 22, the moisture measurement sensor 24, and the weight measurement sensor 26 are connected to an I/O device (input/output device) 94 of the tractor 8 via external wiring 98. In addition to the I/O device 94 and the position sensor 20 which is described above, the tractor 8 further includes a controller 90, a memory 92, and a bus 96 connecting the controller 90, the memory 92, and the I/O device 94. I/O device 94 includes an I/O interface for transmitting and receiving signals to/from the volume measurement sensor 22, the moisture measurement sensor 24, and the weight measurement sensor 26. The I/O interface includes, for example, serial interfaces such as RS-232C and USB, and parallel interfaces such as SCSI. The external wiring 98 is connected to the I/O interface.

The I/O device 94 further includes an I/O interface for writing data in a data transferring device 5. Typically, the data transferring device 5 is an external storage medium such as a USB memory or a SD card. Accordingly, the I/O device 94 further includes an I/O interface such as a USB interface, an SD interface, an SDHC interface, or a UHC interface. However, the data transferring device 5 can be a wireless network such as a cellar network, and the I/O device 94 and an I/O device 64 in the external terminal 6, which is described below, can include a wireless communicator for transmitting/receiving data via the wireless network.

The controller 90 includes an electric circuit including a programmable logic controller (PLC) or a central processing unit (CPU). The controller 90 is configured to control the position sensor 20, the volume measurement sensor 22, the moisture measurement sensor 24, and the weight measurement sensor 26. For example, at least one sensor of the volume measurement sensor 22, the moisture measurement sensor 24, and the weight measurement sensor 26 can have its own clock, and the controller is configured to transmit an NTP signal in accordance with Network Time Protocol via the I/O device to the at least one sensor in order to synchronize a time of the clock of the at least one sensor with a time of the position sensor (e.g. a time in the positioning signal or a time managed by the controller 90). The controller 90 is configured to finally output measurement data sent from the volume measurement sensor 22, the moisture measurement sensor 24, and the weight measurement sensor 26 to the data transferring device 5 via the I/O device 94.

The memory 92 is configured to temporarily or permanently store data sent from the position sensor 20, the volume measurement sensor 22, the moisture measurement sensor 24, and the weight measurement sensor 26 in order for the controller 90 to process them. The memory 92 can store control programs and control data for controlling the tractor 8. Alternatively, the control programs and the control data can be stored in an internal memory of the controller 90. The controller 90 is configured to control movements of the tractor 8 and the connecting unit 85 based on the control programs and the control data as well as in accordance with an operation input form an operator who drives the tractor.

The external terminal 6 is, for example, a device such as a personal computer owned by an administrator who manages a crop material. Note that the external terminal 6 may be a portable terminal such as a smartphone, a tablet, a personal digital assistant (PDA), or may be a server or the like. In addition to the I/O device 64, which is described above, the external terminal 6 further includes a processor 60, a memory 62, a display 66, and a bus 68 connecting the processor 60, the memory 62, the I/O device 64, and the display 66. That is, the yield calculation system 1 further includes the processor 60 and the memory 62. The I/O device 64 includes an I/O interface for reading data from the data transferring device 5. As with the I/O device 94, the I/O device 64 includes an I/O interface such as a USB interface, an SD interface, an SDHC interface, or a UHC interface. If the data transferring device 5 is the wireless network such as a cellar network, the I/O device 64 can include a wireless communicator for transmitting/receiving data via the wireless network.

The processor 60 is, for example, an electric circuit (circuitry) such as a CPU. The memory 62 includes a nonvolatile memory configured to store data permanently. The memory 62 stores a yield calculation program 70, an external information obtaining program 71, and a map generation program 72. The processor 60 is configured to read these programs from the memory 62 and to execute the read programs. The memory 62 also stores raked track data 74 that the processor is configured to read when the processor 60 executes the map generation program 72. In this way, the yield calculation method and the yield map generation method according to the embodiment can be materialized. The display 66 is, for example, a liquid crystal display and is configured to display a yield in each place in the field that is calculated with the yield calculation method according to the embodiment, or a yield map that is created with the yield map generation method according to the embodiment.

Hereinafter, details of the yield calculation method and the yield map generation method according to the embodiment are described. At first, details of the measurement data of the position sensor 20, the volume measurement sensor 22, the moisture measurement sensor 24, and the weight measurement sensor 26, which are sent via the data transferring device 5, are explained. The measurement data has a data format in which each of measurement results of the volume measurement sensor 22, the moisture measurement sensor 24, and the weight measurement sensor 26 is correlated with a position measured by the position sensor 20. For example, the measurement data has arrays or list structure in which (time, a position (latitude, longitude) of the harvester 4, a volume of the bale B1, a moisture weight ratio, a weight of the bale B1) are correlated and stored. Note that all of positions of the harvester 4, volumes of the bale B1, moisture weight ratios, and weights of the bale B1 do always not need to be stored in the measurement data. For example, since the weight of the bale B1 are measured only when the volume of the bale B1 amounts to the reference volume, it is enough to store the volume of the bale B1 at the time. Furthermore, when at least one of the position of the harvester 4, the volume of the bale B1, and the moisture weight ratio is not measured at a certain time, the controller 90 or the processor 60 can calculate an estimated value at the certain time from the measurement results before and after the certain time by publicly known interpolation method.

Further note that the predetermined cycle, which is described above, can be a period between a time at which a combination of the position of harvester 4, the volume of the bale B1, and the moisture weight ratio is measured and a next time at which the combination is measured. Alternatively, all data of the volumes of the bale B1 and the moisture weight ratios which are measured during a period can be treated as data in one cycle, the period being from a certain time at which a previous position of the bale B1 has been measured to a time at which the position of the bale B1 which is a predetermined distance far from the position of the bale B1 is measured.

Figure 4:
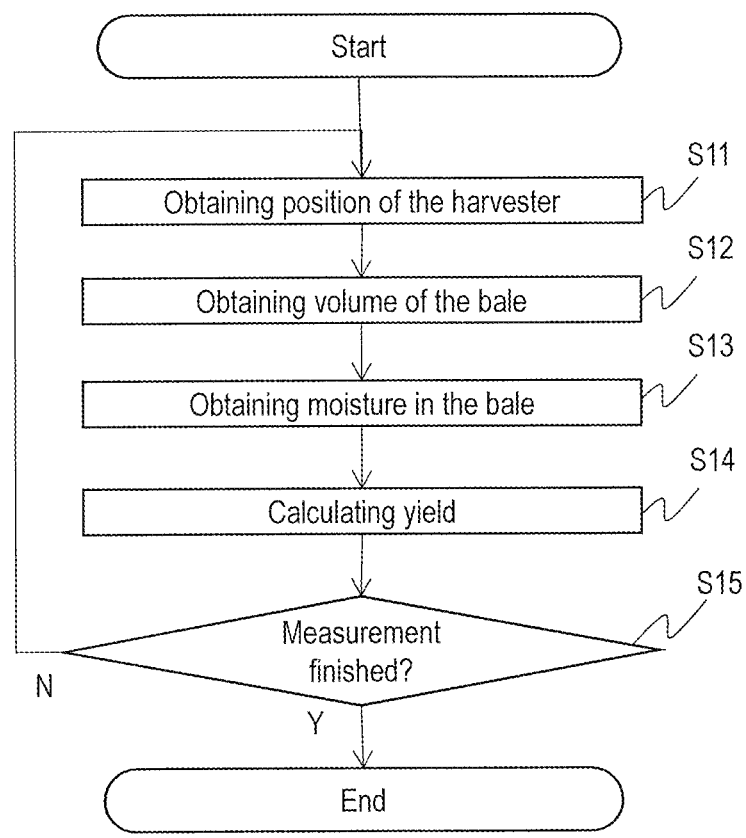
FIG. 4 is a flow chart of a yield calculation method by means of the yield calculation system according to the embodiment as well as a yield calculation program according to the embodiment.

FIG. 4 is a flow chart of a yield calculation method by means of the yield calculation system 1 according to the embodiment as well as the yield calculation program 70 according to the embodiment. The yield calculation program 70 is a computer program including instructions which, when executed by a computer (the external terminal 6), cause the computer (the external terminal 6) to carry out the yield calculation method shown in the flow chart.

In Step S11 in FIG. 4, in the yield calculation method, a position at which the baler 10 harvests a crop material is obtained. While the processor 60 executes the yield calculation program 70, the processor 60 obtains a position at which the baler 10 harvests a crop material. The position has been measured by the position sensor 20 provided on at least one of the baler 10 and the tractor 8 configured to move the baler 10. Accordingly, in the Step S11, a position of the harvester 4 is obtained. Specifically, while the processor 60 executes the yield calculation program 70, the processor 60 reads a position of the harvester 4 in one cycle from the measurement data sent from the data transferring device 5.

In Step S12, in the yield calculation method, a volume of the bale B1 into which the crop material is formed in the bale chamber 14 of the baler 10 is obtained, the volume of the bale B1 corresponding to the position. While the processor 60 executes the yield calculation program 70, the processor 60 obtains a volume of the bale B1 into which the crop material is formed in the bale chamber 14 of the baler 10, the volume of the bale B1 corresponding to the position. Since a width of the roll shape of the bale B1 is defined by internal walls of the bale chamber 14, the volume of the bale B1 is obtained by measuring a diameter of the bale B1 by the volume measurement sensor 22. Specifically, while the processor 60 executes the yield calculation program 70, the processor 60 reads, from the measurement data sent from the data transferring device 5, the volume of the bale B1 in the same cycle as that in Step S11. Furthermore, in the Step S12, while the processor 60 executes the yield calculation program 70, the processor 60 calculates an increment of the volume of the bale B1 from the volume of the bale B1 in the preceding cycle. When there are multiple volumes of the bale B1 in the same cycle as that in Step S11, the processor 60 calculates the increment by using the maximum volume among the multiple volumes.

In Step S13, in the yield calculation method, a moisture amount in the bale B1 is obtained, the moisture amount corresponding to the position. While the processor 60 executes the yield calculation program 70, the processor 60 obtains a moisture amount in the bale B1, the moisture amount corresponding to the position. As described above, the moisture amount is represented by the moisture weight ratio indicating a ratio of a moisture weight in the increment to the weight of the increment. Specifically, while the processor 60 executes the yield calculation program 70, the processor 60 reads, from the measurement data sent from the data transferring device 5, a moisture weight ratio in the same cycle as that in Step S11. When there are multiple moisture weight ratios in the same cycle as that in Step S11, the processor 60 obtains an average of the multiple moisture ratios as the moisture weight ratio in this cycle. Alternatively, the processor 60 can obtain as the moisture weight ratio in this cycle, a moisture ratio that is measured at the time when the maximum volume is measured in the Step S12, or a time closest to the time when the maximum volume is measured in the Step S12.

In Step S14, in the yield calculation method, the yield corresponding to the position is calculated based on the volume of the bale B1 and the moisture amount corresponding to the position by excluding the moisture amount from an amount of the bale B1. While the processor 60 executes the yield calculation program 70, the processor 60 calculates, based on the volume of the bale B1 and the moisture amount corresponding to the position, a yield corresponding to the position by excluding the moisture amount from an amount of the bale B1. The amount of the bale B1 is a weight of an increment of the volume of the bale B1 in the predetermined cycle. In the yield calculation method, the yield is calculated in the predetermined cycle. That is, while the processor 60 executes the yield calculation program 70, the processor 60 calculates the yield in the predetermined cycle.

Specifically, the memory 62 stores a reference unit volume weight indicating a unit volume weight of a remainder obtained by excluding the moisture amount from the amount of the bale B1. The reference unit volume weight is set to an appropriate value based on scientific literature or statistical information, etc. as an initial value. In the yield calculation method, a reference unit volume weight is obtained, the reference unit volume weight indicating a unit volume weight of a remainder obtained by excluding the moisture amount from the amount of the bale B1. More specifically, while the processor 60 executes the yield calculation program 70, the processor 60 reads the reference unit volume weight from the memory 62.

Next, in the yield calculation method, the yield is calculated in the predetermined cycle from the volume of the bale B1, the moisture weight ratio, and the reference unit volume weight, the yield indicating a remaining weight obtained by excluding the moisture weight from the weight of the increment. The yield is calculated using the following equation:

$$G_i = \rho_R \times V_i / \{1 + M_i \times 10^{-2} \times (\rho_R / \rho_W - 1)\},$$

where: $\rho_R$ is the reference unit volume weight [kg/m3]; $\rho_W$ is a unit volume weight of water [kg/m3]; $V_i$ is an i-th increment of the volume of the bale [m$^3$], the i-th increment being the increment measured at in an i-th cycle time (i is an integer); $M_i$ is a percentage of the moisture weight ratio in the i-th increment [wt %] ($M_i$ corresponds to $V_i$); and $G_i$ is an i-th yield [kg] ($G_i$ corresponds to $V_i$).

More specifically, while the processor 60 executes the yield calculation program 70, the processor 60 calculates the yield in the predetermined cycle from the volume of the bale B1, the moisture weight ratio, and the reference unit volume weight, using the above equation.

Finally, in Step S15, in the yield calculation method, whether measurement is finished is determined. Specifically, while the processor 60 executes the yield calculation program 70, the processor 60 determines whether all of the measurement data sent form the data transferring device 5 are read. If all of the measurement data has not been read (No in the Step S15), the yield calculation method returns to the Step S11, then a position of the harvester 4 in the next cycle is read. If all of the measurement data has been read (Yes in the Step S15), the yield calculation method ends. Specifically, the processor 60 finishes executing the yield calculation program 70.

Figure 5:
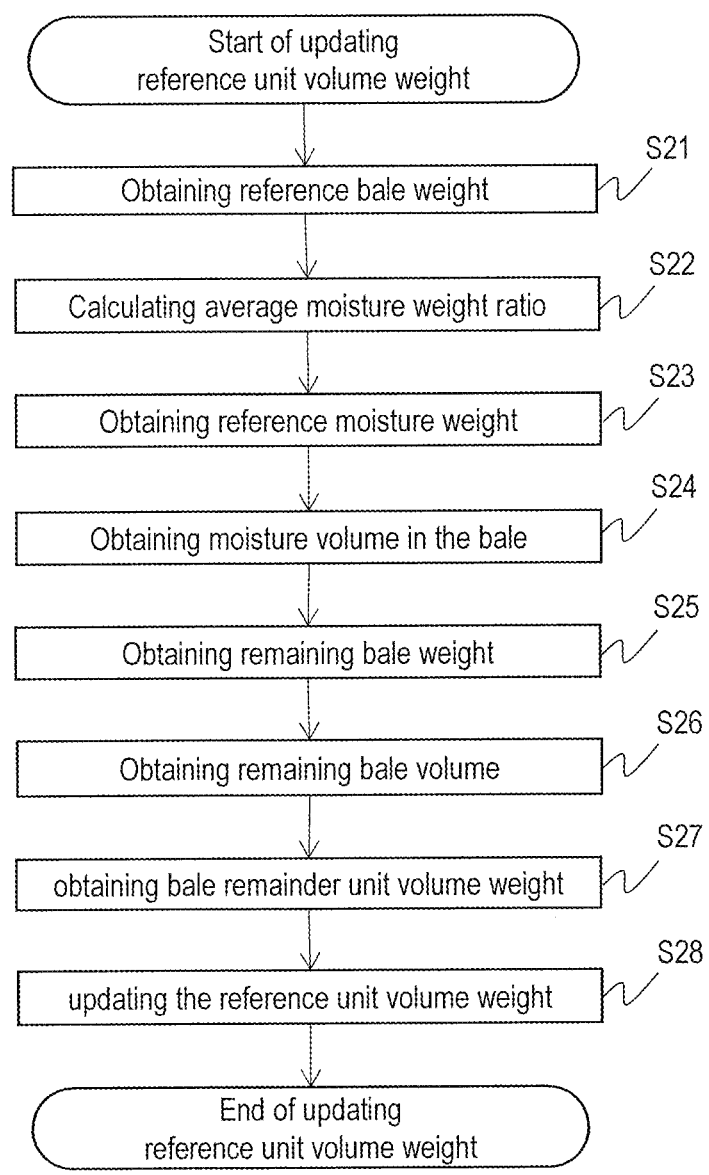
FIG. 5 is a flow chart of a method of updating the reference unit volume weight in the yield calculation method by means of the yield calculation system according to the embodiment as well as the yield calculation program according to the embodiment.

The reference unit volume weight, which is described above, can be updated by using the reference bale weight measured by the weight measurement sensor 26. FIG. 5 is a flow chart of a method of updating the reference unit volume weight in the yield calculation method by means of the yield calculation system according to the embodiment as well as the yield calculation program according to the embodiment. Processes of updating the reference unit volume weight is executed in parallel with the processes shown in FIG. 4. Note that these processes can be omitted from the yield calculation method, the yield calculation system 1, and the yield calculation program 70.

In Step S21 in FIG. 5, in the yield calculation method, the reference bale weight is obtained, the reference bale weight indicating a weight of the reference volume of the bale B1. Specifically, while the processor 60 executes the yield calculation program 70, the processor 60 reads, from the measurement data sent from the data transferring device 5, the reference bale weight as well as a time corresponding to the reference bale weight or a position of the harvester 4 which corresponds to the reference bale weight.

In Step S22, in the yield calculation method, an average moisture weight ratio in the reference volume of the bale B1 is calculated based on the moisture weight ratio obtained in the predetermined cycle. While the processor 60 executes the yield calculation program 70, the processor 60 calculates an average moisture weight ratio in the reference volume of the bale B1 based on the moisture weight ratio measured in the predetermined cycle. Specifically, the processor 60 calculated, as the average moisture weight ratio, an average value of all of the moisture weight ratios measured during a period from a time at which the reference bale weight has been measured at a previous time to a time at which the reference bale weight is measured at a present time (in other words a period from a time at which forming of the bale B1 has been started to a time at which the volume of the bale B1 amounts to the reference volume).

In Step S23, in the yield calculation method, a reference moisture weight indicating a moisture weight in the reference volume of the bale B1 is obtained by multiplying the reference bale weight by the average moisture weight ratio. While the processor 60 executes the yield calculation program 70, the processor 60 obtains a reference moisture weight indicating a moisture weight in the reference volume of the bale B1 by multiplying the reference bale weight by the average moisture weight ratio. Here, let $W_j$, aveM$_j$, and MW$_j$ a is an integer which is more than or equal to 1; j is incremented by 1 every time the reference bale weight is measured) be the reference bale weight [kg], the average moisture weight ratio [wt %], and reference moisture weight [kg], respectively. Then, MW$_j$ is equal to W$_j$×aveM$_j$/100.

In Step S24, in the yield calculation method, a moisture volume in the reference volume of the bale B1 is obtained by dividing the reference moisture weight by a unit volume weight of water. While the processor 60 executes the yield calculation program 70, the processor 60 obtains a moisture volume in the reference volume of the bale B1 by dividing the reference moisture weight by a unit volume weight of water. Here, let MW$_j$, MV$_j$ (j is defined above), and $\rho_W$ be the reference moisture weight [kg], the moisture volume [m$^3$], and the unit volume weight of water [kg/m$^3$], respectively. Then, MV$_j$ is equal to MW$_j$/$\rho_W$.

In Step S25, in the yield calculation method, a remaining bale weight in the reference volume of the bale B1 is obtained by subtracting the reference moisture weight from the reference bale weight. While the processor 60 executes the yield calculation program 70, the processor 60 obtains a remaining bale weight in the reference volume of the bale B1 by subtracting the reference moisture weight from the reference bale weight. Here, let $W_j$, $MW_j$, and $GW_j$ (j is defined above) be the reference bale weight [kg], the reference moisture weight [kg], and the remaining bale weight [kg], respectively. Then, $GW_j$ is equal to $W_j - MW_j$.

In Step S26, in the yield calculation method, a remaining bale volume in the reference volume of the bale B1 is obtained by subtracting the moisture volume from the reference volume. While the processor 60 executes the yield calculation program 70, the processor 60 obtains a remaining bale volume in the reference volume of the bale B1 by subtracting the moisture volume from the reference volume. Here, let $V_j$, $MV_j$, and $GV_j$ (j is defined above) be the reference volume [m³], the moisture volume [m³], and the remaining bale volume [m³], respectively. Then, $GV_j$ is equal to $V_j - MV_j$.

In Step S27, in the yield calculation method, a bale remainder unit volume weight is obtained by dividing the remaining bale weight by the remaining bale volume. While the processor 60 executes the yield calculation program 70, the processor 60 obtains a bale remainder unit volume weight by dividing the remaining bale weight by the remaining bale volume. Here, let $GW_j$, $GV_j$, and $\rho_j$ (j is defined above) be the remaining bale weight [kg], the remaining bale volume [m³], and the bale remainder unit volume weight [kg/m³], respectively. Then, $\rho_j$ is equal to $GW_j/GV_j$.

In Step S28, in the yield calculation method, the reference unit volume weight is updated based on the reference volume, the average moisture weight ratio, and the reference bale weight. While the processor 60 executes the yield calculation program 70, the processor 60 updates the reference unit volume weight based on the reference volume, the average moisture weight ratio, and the reference bale weight. Specifically, in the yield calculation method, the reference unit volume weight and the bale remainder unit volume weight are weighted averaged to obtain the reference unit volume weight updated. While the processor 60 executes the yield calculation program 70, the processor 60 weighted averages the reference unit volume weight and the bale remainder unit volume weight to obtain the reference unit volume weight updated.

Here, let j in $\rho_j$ be an integer which is more than or equal to 0, and let $\rho_0$ be the initial value of the reference unit volume weight [kg/m³]. Then, let $\alpha_j$ ($\alpha_j$ is a real number which is more than or equal to 0 and less than or equal to 1) be a weight corresponding to $\rho_j$, and let $\rho_R$ be an updated reference unit volume weight [kg/m³] after the reference bale weight is measured at N-th time (N is an integer larger than 1). In this time, $\rho_R$ is calculated by the following equation:

$$\rho_R = \sum_{j=0}^{N} \alpha_j \cdot \rho_j \left( \text{where} \sum_{j=0}^{N} \alpha_j = 1 \right)$$

Supposing $\alpha_0$ is set to 0 in the above equation, it is possible to set $\rho_R$ based on only measured values by eliminating the effect of the initial value. Alternatively, supposing all of $\alpha_j$ are 1/N, $\rho_R$ can be set to a simple mean average of $\rho_0$ to $\rho_N$. Furthermore, the processor 60 can execute the external information obtaining program 71 to obtain, from a server of the weather information provider, weather during a period between a day when the crop material has been mowed and a day when the crop material has been harvested, to increase the weight if good weather has continued during the period, and to decrease the weight as rainfall days increase during the period. In a case where such change of the weight is not performed, it is possible to omit the external information obtaining program 71.

As shown in FIG. 1, the yield map generation system 2 includes the yield calculation system 1, and the memory 20 stores the map generation program 72 and the raked track data 74. The map generation program 72 is a computer program including instructions which, when executed by a computer (the external terminal 6), cause the computer (the external terminal 6) to carry out a method of generating a yield map for the baler 10. The method of generating a yield map for the baler 10 includes the yield calculation method, which is described above, and generating a yield map in which the yield is correlated with the position detected in the predetermined cycle. The map generation program 72 can include instructions which cause the computer (the external terminal 6) to call the yield calculation program 70 in order for the computer (the external terminal 6) to carry out the yield calculation method. Alternatively, the map generation program 72 can include a structure of the yield calculation program 70. While the processor 60 executes the map generation program 72, the processor 60 generates a yield map in which the yield is correlated with the position detected in the predetermined cycle.

Figure 6:
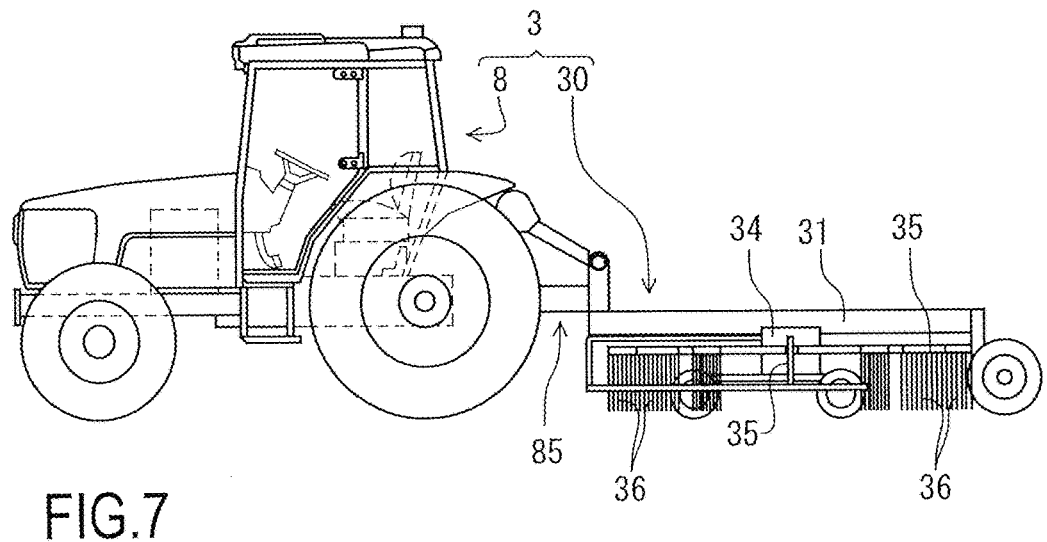
FIG. 6 is a side view of a raking machine.
Figure 7:
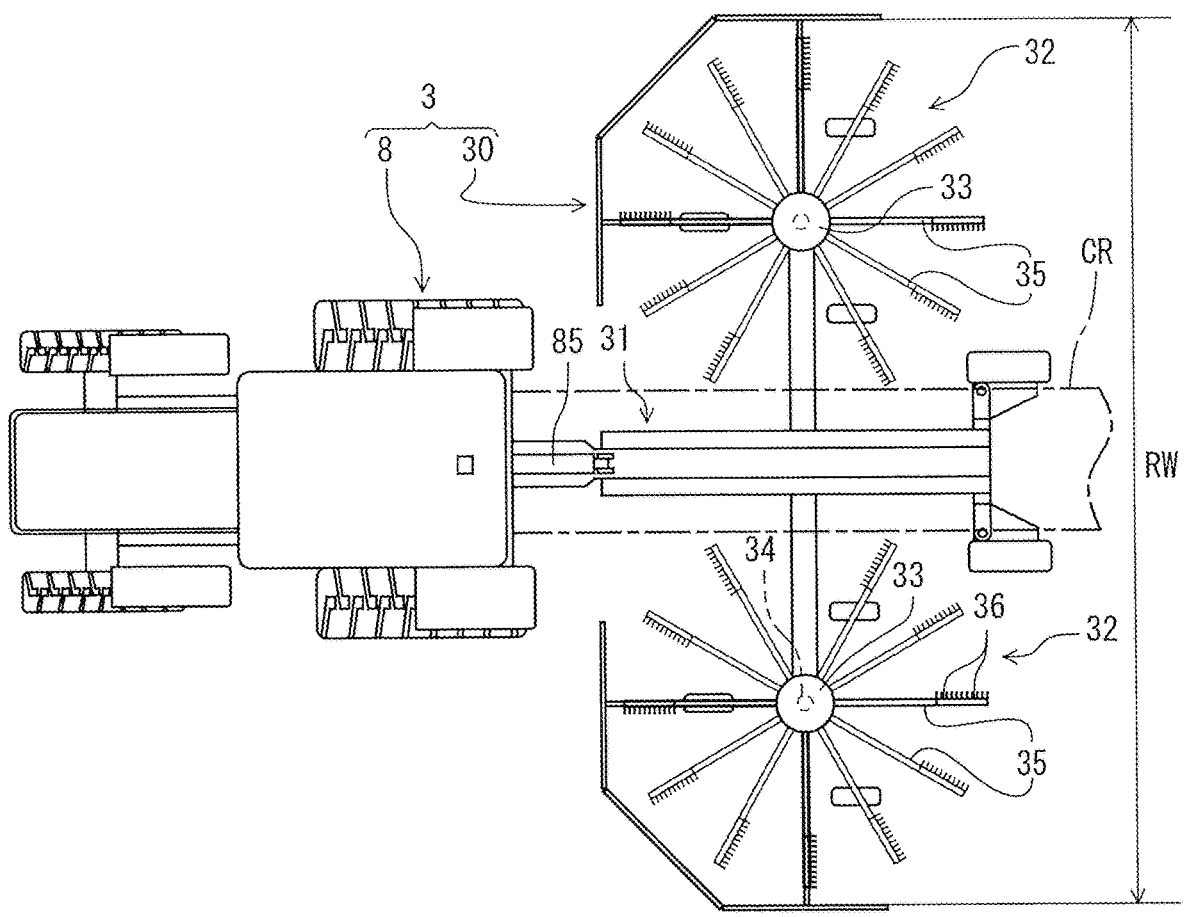
FIG. 7 is a plan view of the raking machine.

Next, details of the method of generating the yield map is described. The yield map is a map showing yields in regions into which an area of the field is divided based on a raked track in the area. So, at first, how the raked track is generated is described. Upon harvesting the crop material, the crop material is first mowed by a mower, then the mowed material is spread over the field by a tedder. The spread crop material is dried by sun drying. The dried material is gathered to parts of the field by a raking machine 3. FIGS. 6 and 7 are a side view and a plan view of the raking machine 3, respectively.

Referring to FIGS. 6 and 7, the raking machine 3 includes the tractor 8 and a raking implement 30. Here, the tractor 8 has the same configuration as that of the tractor 8 of the harvester 4, thereby the detailed description is omitted. The raking implement 30 includes a connecting frame 31 connected to the connecting unit 85 of the tractor 8, and raking units 32 connected to the connecting frame 31. Note that FIG. 7 illustrates an example in which two raking units 32 are connected to the connecting frame 31.

The raking units 32 each include a body 33 connected to the connecting frame 31, a rotating shaft 34 rotatably supported by the body 33, a plurality of arms (tine arms) 35 connected to the rotating shaft 34, and raking tools (tines) 36 connected to the plurality of arms 35. The tine 36 has, for example, a structure in which inverse-U shaped members are arranged in a longitudinal direction of the arm 35. The power of the PTO shaft is transmitted to the rotating shaft 34 via a driving shaft supported by the connecting frame 31, thereby rotating the rotating shaft 34. As the rotating shaft 34 rotates, the arms 35 rotate, and the raking tools 36 gathers the crop material about the connecting frame 31. FIG. 7 depicts one dot chain lines to show a region CR about which the crop material is gathered.

Note that the raking implement 30 is not limited to the above-described configuration. For example, one raking unit 32, or three or more raking units 32 may be provided. The region CR about which the crop material is gathered by the raking units 32 is not limited to a central portion of the raking implement 30. It may be a right end or a left end of the raking implement 30. Also, the raking unit 32 may be a rotary type in which a rotor with the raking tools 36 rotates around a longitudinal axis, may be a belt/chain type in which the plurality of raking tools 36 is attached to a rotating belt or chain, or may be any other type.

Figure 8:
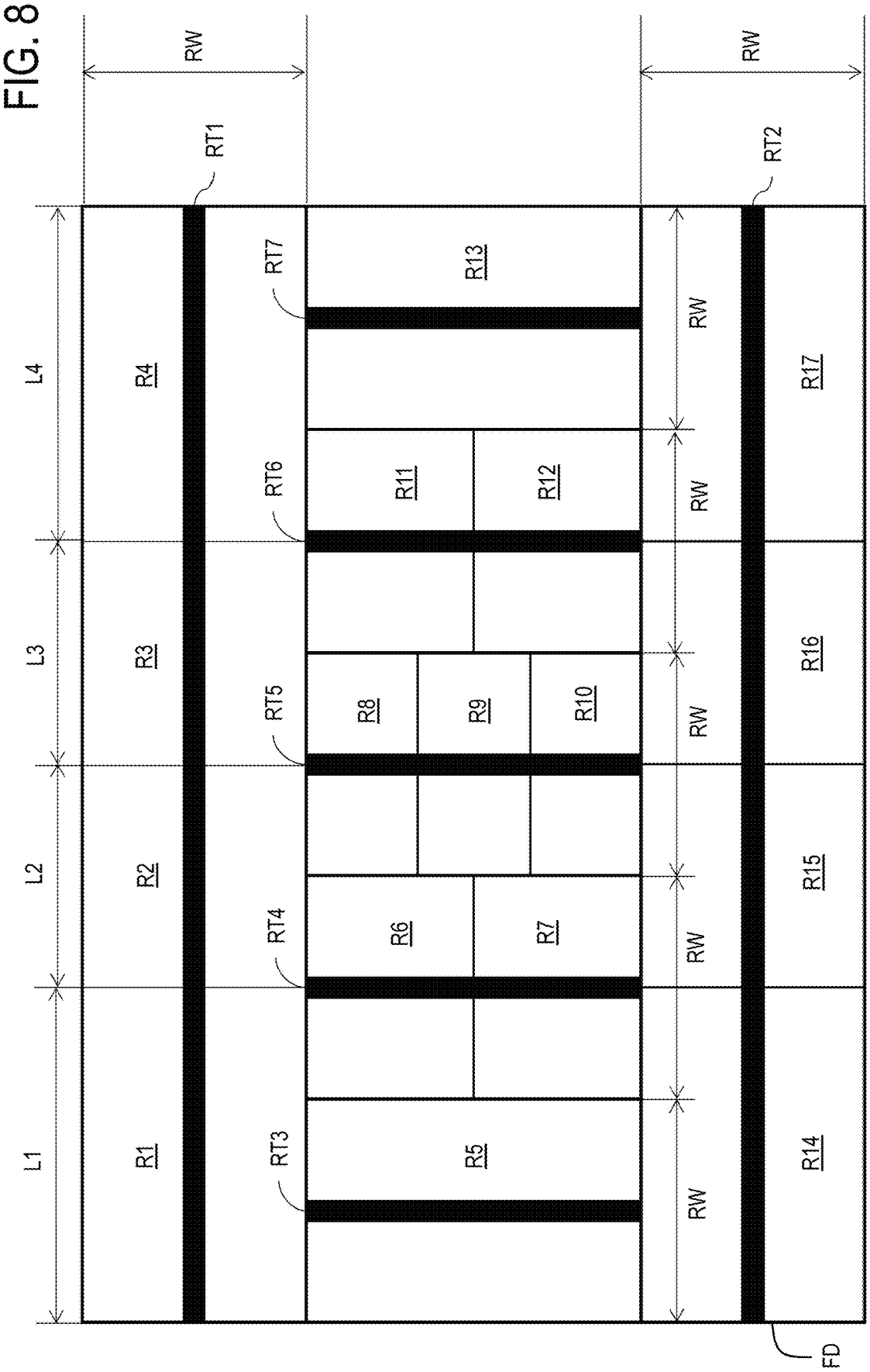
FIG. 8 is an example of raked tracks.

FIG. 8 shows an example of raked tracks RT1 to RT7 in the field FD, the raked tracks RT1 to RT7 having been generated by gathering the crop material about the region CR. The harvester 4 forms the bale B1 by traveling along the raked tracks RT1 to RT7. That is, the baler 10 travels along the raked tracks RT1 to RT7 to form the bale B1. In a case where the raking implement 30 has a structure to gather the crop material about its central part, the crop material having existed in an area is gathered about each of the raked tracks RT1 to RT7, the area having a width in a width direction perpendicular to a lengthwise direction of each of the raked tracks RT1 to RT7 such that each of the raked tracks RT1 to RT7 is in a middle of the area in the width direction, the width being equal to a width RW of the raking implement 30 (See FIG. 7). Note that depending on a structure of the raking implement 30, the crop material having existed in an area may be gathered about each of the raked tracks RT1 to RT7, the area having a width in the width direction such that each of the raked tracks RT1 to RT7 is in a left end or a right end of the area in the width direction, the width being equal to a width RW of the raking implement 30. The memory 62 stores positions and dimensions of the raked tracks RT1 to RT7 as the raked track data 74. Furthermore, the memory 62 can store a map information of the field FD as the raked track data 74. Note that the map information of the field FD may be generated by a user in advance or may be generated based on a movement locus of the raking machine 3.

Figure 9:
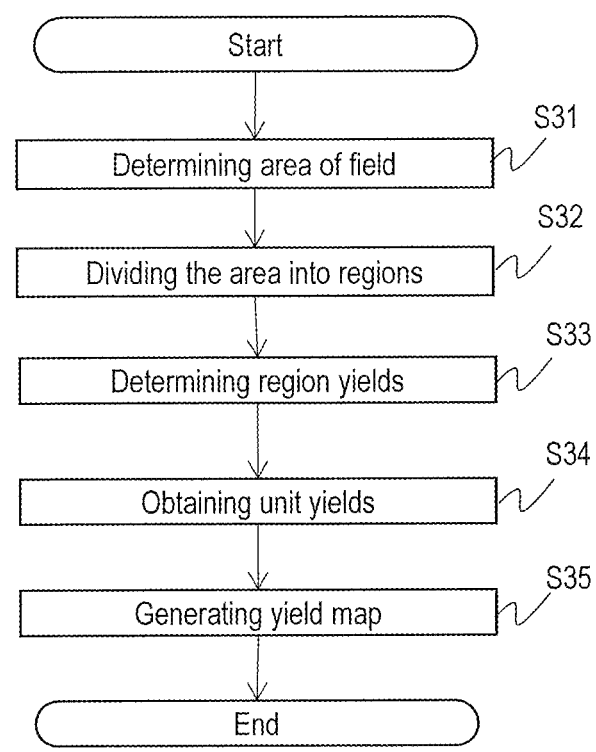
FIG. 9 is a flow chart of a method of generating a yield map by means of the yield map generation system according to the embodiment as well as the map generation program according to the embodiment.

In the following, a method of generating a yield map by means of the yield map generation system 2 as well as processes executed by the map generation program 72 are described. FIG. 9 is a flow chart of a method of generating a yield map by means of the yield map generation system 2 according to the embodiment as well as the map generation program 72 according to the embodiment.

In Step S31 in FIG. 9, in the yield map generation method, an area of the field FD is determined. Specifically, while the processor 60 executes the map generation program 72, the processor 60 determines an area of the field FD with the following (1) or (2) method, for example. (1) The processor 60 reads the map information of the field FD from the memory 62. (2) The processor 60 aggregates the positions detected by the position sensor 20 to obtain a movement locus of the baler 10 (or the tractor 8), and then determine that an area having the width RW of the raking implement 30 in the width direction along the movement locus is the area of the field FD.

In Step S32, in the yield map generation method, the area is divided into regions R1 to R17 based on the raked tracks RT1 to RT7 in the area. While the processor 60 executes the map generation program 72, the processor 60 divides the area into regions R1 to R17 based on the raked tracks RT1 to RT7 in the area. Note that a number of regions is arbitrary, and 17 is a mere example. Widths of these regions R1 to R17 are equal to the width RW of the raking implement 30. However, lengths of the regions R1 to R17 in their respective lengthwise directions perpendicular to their respective widths are arbitrary. (Here, a length of a region indicates a length of region in the lengthwise direction.) FIG. 8 shows lengths of the regions R1 to R4 as L1 to L4, respectively. In FIG. 8, the area of the field FD is divided into the regions R1 to R17 such that lengths of the regions R1 to R17 is shorter as the regions R1 to R17 are closer to a center of the field FD. However, the divisional method is not limited to such method. The lengths of all regions can be the same, or lengths of regions can be determined in accordance with the sampling time. Alternatively, in a specific area of the field FD in which a user would like to know yield in detail, lengths of the regions can be short, and many regions can be provided in the specific area.

In Step S33, in the yield map generation method, region yields in the regions R1 to R17 are determined, respectively, by correlating, with one of the regions R1 to R17, the yield calculated in the predetermined cycle. While the processor 60 executes the map generation program 72, the processor 60 determines region yields in the regions R1 to R17, respectively, by correlating, with one of the regions R1 to R17, the yield calculated in the predetermined cycle. Specifically, while the processor 60 executes the map generation program 72, the processor 60 determines which of the regions R1 to R17 the position corresponding to the yield calculated in the Step S14 exists in. Then, the processor 60 determines, as the region yield in each of the regions R1 to R17, a sum of yields corresponding to positions that exist in each of the regions R1 to R17.

In Step S34, in the yield map generation method, region yields are divided by dimensions of the regions R1 to R17, respectively, to obtain unit yields in the regions R1 to R17, respectively. While the processor 60 executes the map generation program 72, the processor 60 divide region yields by dimensions of the regions R1 to R17, respectively, to obtain unit yields in the regions R1 to R17, respectively. Here, let $Y_k$, $S_k$, and $UY_k$ be the region yield [kg] of the region $R_k$, the dimensions [m$^2$] of the region $R_k$, and the unit yield [kg/m$^2$] of the region $R_k$ (where k is an integer; $R_1$ to $R_{17}$ correspond to R1 to R17, respectively). Then, $UY_k$ is equal to $Y_k/S_k$.

Figure 10:
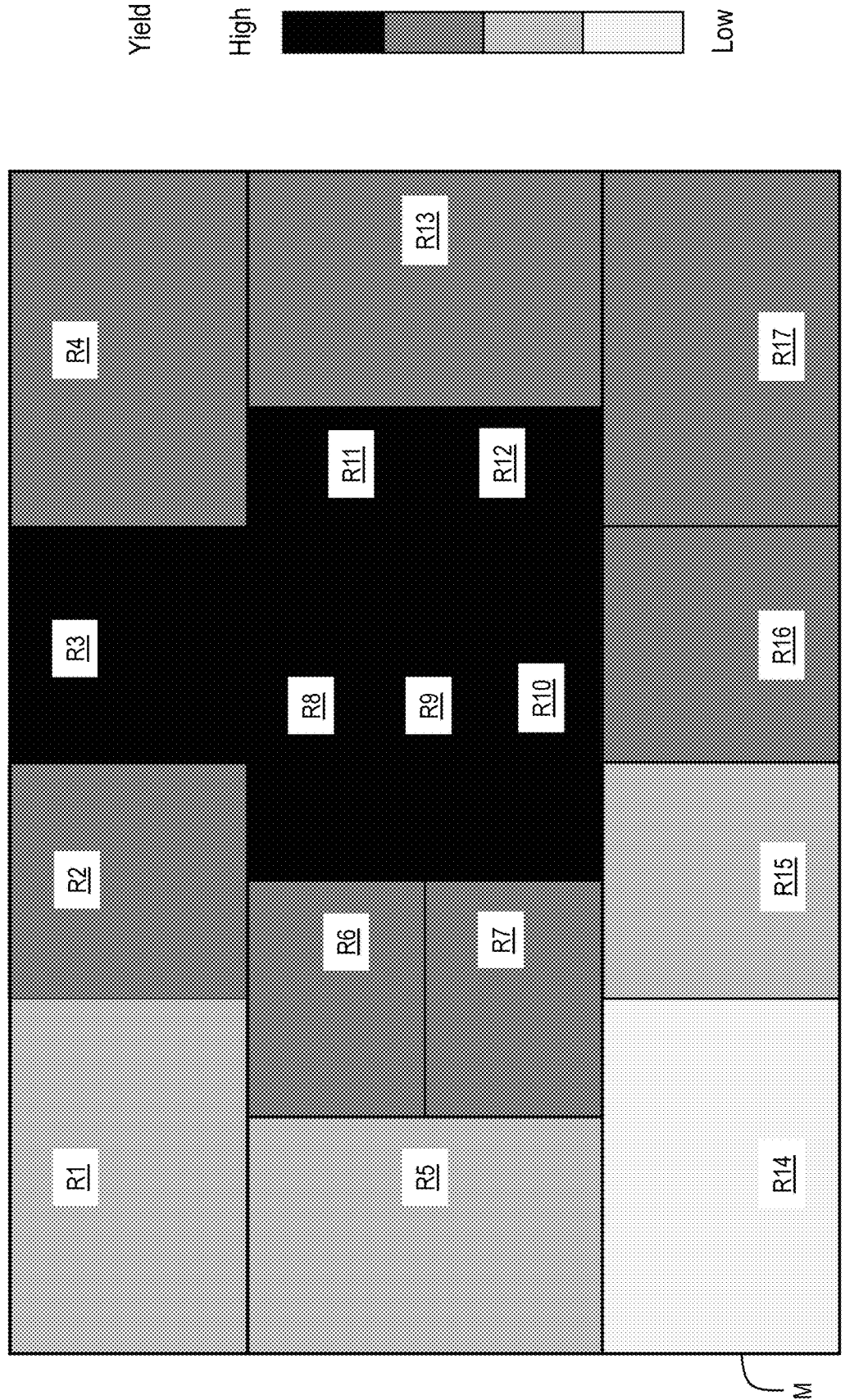
FIG. 10 illustrates an example of the yield map.

In Step S35, in the yield map generation method, a yield map in which the regions R1 to R17 are correlated with yield levels calculated based on the unit yields, respectively, is generated. While the processor 60 executes the map generation program 72, the processor 60 generates a yield map in which the regions R1 to R17 are correlated with yield levels calculated based on the unit yields, respectively. More specifically, while the processor 60 executes the map generation program 72, the processor 60 calculates the yield level based on which of predetermined ranges the unit yield $UY_k$ falls in. For example, the processor 60 sets the yield level to 1 when the unit yield $UY_k$ is equal to or larger than 0 and less than TH1, sets the yield level to 2 when the unit yield $UY_k$ is equal to or larger than TH1 and less than TH2, sets the yield level to 3 when the unit yield $UY_k$ is equal to or larger than TH2 and less than TH3, and sets the yield level to 4 when the unit yield $UY_k$ is equal to or larger than TH3 (where 0<TH1<TH2<TH3). FIG. 10 shows an example of the yield map M that the processor 60 generates. In the yield map M, the regions R1 to R17 are shown such that colors, textures, figures, letters, numbers etc. indicating the regions R1 to R17 are changed in accordance with the yield levels of the regions R1 to R17.

Modifications of the Embodiment

That's all of the basic description of the yield map generation system 2 (the yield calculation system 1), the yield map generation method (the yield calculation method), and the map generation program 72 (the yield calculation program 70). However, the yield map generation system 2

(the yield calculation system 1), the yield map generation method (the yield calculation method), and the map generation program 72 (the yield calculation program 70) are not limited to those described in the above embodiment. For example, the memory 92 may store the yield calculation program 70, and the controller 90 may execute the yield calculation program 70. Furthermore, the memory 92 may store the yield calculation program 70 and the map generation program 72, and the controller 90 may execute the yield calculation program 70 and the map generation program 72. In these cases, the yield map generation system 2 (the yield calculation system 1), the external terminal 6 can be omitted. In a case where the data transferring device 5 is the wireless network, the processor may calculate the yield in real time. In a case where the processor 60 determines the area of the field by aggregating the positions detected by the position sensor 20, the raked track data 74 can be omitted.

Partial functions of the volume measurement sensor 22, the moisture measurement sensor 24, and the weight measurement sensor 26 can be realized by the controller 90. For example, the controller 90 can attach times to measurement values of the volume measurement sensor 22, the moisture measurement sensor 24, and the weight measurement sensor 26. At least one sensor of the volume measurement sensor 22, the moisture measurement sensor 24, and the weight measurement sensor 26 can be configured to conduct measurement in response to an input of a trigger signal and output a measurement data to the external wiring 98. In this case, the controller 90 is configured to transmit, via the I/O device 94, the trigger signal to the at least one sensor in response to a reception of a signal from the position sensor 20 and to attach a time of the signal from the position sensor 20 to the measurement data sent from the at least one sensor. Furthermore, the controller 90 or the processor 60 can convert the measurement value of the volume measurement sensor 22 to the volume of the bale B1. The controller 90 or the processor 60 can convert the measurement value of the moisture measurement sensor 24 to the moisture weight ratio. The controller 90 or the processor 60 can convert the measurement value of the weight measurement sensor 26 to the reference bale weight. In the cases where part of functions of the volume measurement sensor 22, the moisture measurement sensor 24, and the weight measurement sensor 26, which are described in the embodiment, is realized by the controller 90 or the processor 60, the volume measurement sensor 22 and the part of functions that are realized by the controller 90 or the processor 60 can be collectively referred to as the volume measurement sensor, the moisture measurement sensor 24 and the part of functions that are realized by the controller 90 or the processor 60 can be collectively referred to as the volume measurement sensor, and the weight measurement sensor 26 and the part of functions that are realized by the controller 90 or the processor 60 can be collectively referred to as the weight measurement sensor.

Partial or all functions of the yield calculation program 70 and the map generation program 72 may be realized by a dedicated processor or an integrated circuit. The yield calculation program 70 and the map generation program 72 can be stored in not only the memory 62 that is built-in the external terminal 6 but also a computer readable storage medium that is detachable from a computer (the external terminal 6) such as a disk including a floppy disk, an optical disk, a CD-ROM, and a magnetic disk, as well as SD-card, an USB memory, or an external hard disk and the like.

Advantageous Effects of the Embodiment

With the yield calculation system 1, the yield calculation method, and the yield calculation program 70 according to the embodiment, the yield in which the moisture amount is excluded from the amount of the bale B1 is calculated. Accordingly, it is possible to calculate a yield which is less subject to a climate.

More specifically, in accordance with a first aspect of the present disclosure, a yield calculation system includes a position sensor configured to detect a position, a baler, and a processor. The baler includes a bale chamber, a volume measurement sensor, and a moisture measurement sensor. The crop material is to be formed into a bale in the bale chamber. The volume measurement sensor is provided in the bale chamber. The volume measurement sensor is configured to measure a volume of the bale in the bale chamber, the volume corresponding to the position detected by the position sensor. The moisture measurement sensor is provided in the bale chamber. The moisture measurement sensor is configured to measure a moisture amount in the bale, the moisture amount corresponding to the position detected by the position sensor. The processor is configured to calculate, based on the volume of the bale and the moisture amount corresponding to the position, a yield corresponding to the position by excluding the moisture amount from an amount of the bale.

In accordance with a second aspect of the present disclosure, the yield calculation system according to the first aspect is configured so that the volume measurement sensor is configured to measure a diameter of the bale.

In accordance with a third aspect of the present disclosure, the yield calculation system according to the first or second aspect further includes a tractor configured to move the baler. The position sensor is provided on at least one of the baler and the tractor.

In accordance with a fourth aspect of the present disclosure, the yield calculation system according to any of the first to third aspects is configured so that the processor is configured to calculate the yield in a predetermined cycle.

In accordance with a fifth aspect of the present disclosure, the yield calculation system according to the fourth aspect is configured so that the predetermined cycle is constituted by at least one of a predetermined time and an amount of change of the position.

In accordance with a sixth aspect of the present disclosure, the yield calculation system according to the fourth or fifth aspect is configured so that the amount of the bale is a weight of an increment of the volume of the bale in the predetermined cycle. The moisture amount is represented by a moisture weight ratio indicating a ratio of a moisture weight in the increment to the weight of the increment.

In accordance with a seventh aspect of the present disclosure, the yield calculation system according to the sixth aspect further includes a memory configured to store a reference unit volume weight indicating a unit volume weight of a remainder obtained by excluding the moisture amount from the amount of the bale. The processor is configured to calculate the yield in the predetermined cycle from the volume of the bale, the moisture weight ratio, and the reference unit volume weight, the yield indicating a remaining weight obtained by excluding the moisture weight in the increment from the weight of the increment.

In accordance with an eighth aspect of the present disclosure, the yield calculation system according to the seventh aspect is configured so that the baler further includes a weight measurement sensor configured to measure a reference bale weight indicating a weight of a reference volume of the bale, when the volume of the bale amounts to the reference volume. The processor is configured to calculate an average moisture weight ratio in the reference volume of the bale based on the moisture weight ratio measured in the predetermined cycle, and update the reference unit volume weight based on the reference volume, the average moisture weight ratio, and the reference bale weight.

In accordance with a ninth aspect of the present disclosure, the yield calculation system according to the eighth aspect is configured so that the processor is configured to obtain a reference moisture weight indicating a moisture weight in the reference volume of the bale by multiplying the reference bale weight by the average moisture weight ratio. The processor is configured to obtain a moisture volume in the reference volume of the bale by dividing the reference moisture weight by a unit volume weight of water. The processor is configured to obtain a remaining bale weight in the reference volume of the bale by subtracting the reference moisture weight from the reference bale weight. The processor is configured to obtain a remaining bale volume in the reference volume of the bale by subtracting the moisture volume from the reference volume. The processor is configured to obtain a bale remainder unit volume weight by dividing the remaining bale weight by the remaining bale volume. The processor is configured to weighted average the reference unit volume weight and the bale remainder unit volume weight to obtain the reference unit volume weight updated.

In accordance with a tenth aspect of the present disclosure, the yield calculation system according to any one of the seventh to ninth aspects is configured so that the processor is configured to calculate the yield using the following equation:

$$G_i = \rho_R \times V_i / \{1 + M_i \times 10^{-2} \times (\rho_R/\rho_W - 1)\},$$

where:
- $\rho_R$ is the reference unit volume weight [kg/m$^3$];
- $\rho_W$ is a unit volume weight of water [kg/m$^3$];
- $V_i$ is an i-th increment of the volume of the bale, the i-th increment being the increment in an i-th cycle [m$^3$] (i is an integer);
- $M_i$ is a percentage of the moisture weight ratio in the i-th increment [wt %] ($M_i$ corresponds to $V_i$); and
- $G_i$ is an i-th yield [kg] ($G_i$ corresponds to $V_i$).

In accordance with an eleventh aspect of the present disclosure, a yield map generation system includes the yield calculation system according to any one of the fourth to tenth aspects. The processor is configured to generate a yield map in which the yield is correlated with the position detected in the predetermined cycle.

In accordance with a twelfth aspect of the present disclosure, a yield map generation system includes the yield calculation system according to any one of the fourth to tenth aspects. The processor is configured to determine an area of a field. The processor is configured to divide the area into regions based on a raked track in the area, the baler being configured to travel along the raked track to form the bale. The processor is configured to determine region yields in the regions, respectively, by correlating, with one of the regions, the yield calculated in the predetermined cycle. The processor is configured to divide region yields by dimensions of the regions to obtain unit yields in the regions, respectively. The processor is configured to generate a yield map in which the regions are correlated with yield levels calculated based on the unit yields, respectively.

In accordance with a thirteenth aspect of the present disclosure, a method of calculating a yield for a baler includes: obtaining a position at which the baler harvests a crop material; obtaining a volume of a bale into which the crop material is formed in a bale chamber of the baler, the volume of the bale corresponding to the position; obtaining a moisture amount in the bale, the moisture amount corresponding to the position; and calculating, based on the volume of the bale and the moisture amount corresponding to the position, the yield corresponding to the position by excluding the moisture amount from an amount of the bale.

In accordance with a fourteenth aspect of the present disclosure, in the method according to the thirteenth aspect, the volume of the bale is obtained by measuring a diameter of the bale.

In accordance with a fifteenth aspect of the present disclosure, in the method according to the thirteenth or fourteenth aspect, the position is obtained by a position sensor provided on at least one of the baler and a tractor configured to move the baler.

In accordance with a sixteenth aspect of the present disclosure, in the method according to any one of the thirteenth to fifteenth aspects, the yield is calculated in a predetermined cycle.

In accordance with a seventeenth aspect of the present disclosure, in the method according to the sixteenth aspect, the predetermined cycle is constituted by at least one of a predetermined time and an amount of change of the position.

In accordance with an eighteenth aspect of the present disclosure, in the method according to the sixteenth or seventeenth aspect, the amount of the bale is a weight of an increment of the volume of the bale in the predetermined cycle. The moisture amount is represented by a moisture weight ratio indicating a ratio of a moisture weight in the increment to the weight of the increment.

In accordance with a nineteenth aspect of the present disclosure, the method according to the eighteenth aspect further comprises obtaining a reference unit volume weight indicating a unit volume weight of a remainder obtained by excluding the moisture amount from the amount of the bale. In the method, the yield is calculated in the predetermined cycle from the volume of the bale, the moisture weight ratio, and the reference unit volume weight, the yield indicating a remaining weight obtained by excluding the moisture weight from the weight of the increment.

In accordance with a twentieth aspect of the present disclosure, the method according to the nineteenth aspect further comprises: obtaining a reference bale weight indicating a weight of a reference volume of the bale; calculating an average moisture weight ratio in the reference volume of the bale based on the moisture weight ratio obtained in the predetermined cycle; and updating the reference unit volume weight based on the reference volume, the average moisture weight ratio, and the reference bale weight.

In accordance with a twenty-first aspect of the present disclosure, the method according to the twentieth aspect further comprises: obtaining a reference moisture weight indicating a moisture weight in the reference volume of the bale by multiplying the reference bale weight by the average moisture weight ratio; obtaining a moisture volume in the reference volume of the bale by dividing the reference moisture weight by a unit volume weight of water; obtaining a remaining bale weight in the reference volume of the bale by subtracting the reference moisture weight from the reference bale weight; obtaining a remaining bale volume in the reference volume of the bale by subtracting the moisture volume from the reference volume; obtaining a bale remainder unit volume weight by dividing the remaining bale weight by the remaining bale volume. In the method, the reference unit volume weight and the bale remainder unit volume weight are weighted averaged to obtain the reference unit volume weight updated.

In accordance with a twenty-second aspect of the present disclosure, in the method according to any one of the nineteenth to twenty-first aspects, the yield is calculated using the following equation:

$$G_i = \rho_R \times V_i / \{1 + M_i \times 10^{-2} \times (\rho_R/\rho_W - 1)\},$$

where:
- $\rho_R$ is the reference unit volume weight [kg/m³];
- $\rho_W$ is a unit volume weight of water [kg/m³];
- Vi is an i-th increment of the volume of the bale [m³], the i-th increment being the increment in an i-th cycle (i is an integer);
- Mi is a percentage of the moisture weight ratio in the i-th increment [wt %] (Mi corresponds to Vi); and
- Gi is an i-th yield [kg] (Gi corresponds to Vi).

In accordance with a twenty-third aspect of the present disclosure, a method of generating a yield map for a baler, comprises: the method according to any one of the sixteenth to twenty-second aspects; and generating a yield map in which the yield is correlated with the position detected in the predetermined cycle.

In accordance with a twenty-fourth aspect of the present disclosure, a method of generating a yield map for a baler, comprises: the method according to any one of the sixteenth to twenty-second aspects; and determining an area of the field; dividing the area into regions based on a raked track in the area, the baler being configured to travel along the raked track to form the bale; determining region yields in the regions, respectively, by correlating, with one of the regions, the yield calculated in the predetermined cycle; dividing region yields by dimensions of the regions to obtain unit yields in the regions, respectively; and generating a yield map in which the regions are correlated with yield levels calculated based on the unit yields, respectively.

Computer programs according to twenty-fifth to thirty-sixth aspects of the present disclosure, comprise instructions which, when executed by a computer, cause the computer to carry out the methods according to thirteenth to twenty-fourth aspects, respectively.

Computer readable storage mediums according to thirty-seventh to forty-eighth aspects of the present disclosure, comprise instructions which, when executed by a computer, cause the computer to carry out the methods according to thirteenth to twenty-fourth aspects, respectively.

With the technology discloses in the present application, more specifically, with the yield calculation system according to the first aspect, the method of calculating a yield for a baler according to the thirteenth aspect, the computer program according to the twenty-fifth aspect, and the computer readable storage medium according to the thirty-seventh aspect, the yield in which the moisture amount is excluded from the amount of the bale is calculated. Accordingly, it is possible to calculate a yield which is less subject to a climate.

With the yield calculation system according to the second aspect, the method of calculating a yield for a baler according to the fourteenth aspect, the computer program according to the twenty-sixth aspect, and the computer readable storage medium according to the thirty-eighth aspect, it is possible to calculate the volume of a baler which has a cylindrical shape.

With the yield calculation system according to the third aspect, the method of calculating a yield for a baler according to the fifteenth aspect, the computer program according to the twenty-seventh aspect, and the computer readable storage medium according to the thirty-ninth aspect, it is possible to flexibly install the position sensor.

With the yield calculation system according to the fourth aspect, the method of calculating a yield for a baler according to the sixteenth aspect, the computer program according to the twenty-eighth aspect, and the computer readable storage medium according to the fortieth aspect, it is possible to calculate the yields at the positions.

With the yield calculation system according to the fifth aspect, the method of calculating a yield for a baler according to the seventeenth aspect, the computer program according to the twenty-ninth aspect, and the computer readable storage medium according to the forty-first aspect, it is possible to calculate the yields at intervals of at least one of a sampling time and a predetermined distance.

With the yield calculation system according to the sixth aspect, the method of calculating a yield for a baler according to the eighteenth aspect, the computer program according to the thirtieth aspect, and the computer readable storage medium according to the forty-second aspect, it is possible to use as the moisture measurement sensor, a spectroscopic sensor to detect a ratio of a weight of a moisture in a sample to a weight of the sample.

With the yield calculation system according to the seventh aspect, the method of calculating a yield for a baler according to the nineteenth aspect, the computer program according to the thirty-first aspect, and the computer readable storage medium according to the forty-third aspect, it is possible to calculate the yield in real time, because the yield is calculated based on the volume of the bale and the moisture weight ratio which can be calculated in real time.

With the yield calculation system according to the eighth aspect, the method of calculating a yield for a baler according to the twentieth aspect, the computer program according to the thirty-second aspect, and the computer readable storage medium according to the forty-fourth aspect, it is possible to calculate the yield with high accuracy, because the reference unit volume is updated when the volume of the bale amounts to the reference volume.

With the yield calculation system according to the ninth aspect, the method of calculating a yield for a baler according to the twenty-first aspect, the computer program according to the thirty-third aspect, and the computer readable storage medium according to the forty-fifth aspect, it is possible to obtain the reference unit volume weight more accurately as the reference unit volume weight is updated. Furthermore, by changing the weight, it is possible to provide an initial value of the reference unit volume weight in a suitable manner and to update the reference unit volume weight based on actual measured values or to prioritize the actual measured values based on climates.

With the yield calculation system according to the tenth aspect, the method of calculating a yield for a baler according to the twenty-second aspect, the computer program according to the thirty-fourth aspect, and the computer readable storage medium according to the forty-sixth aspect, it is possible to calculate the yield at high speed, because the yield is algebraically calculated.

With the yield map generation system according to the eleventh aspect, the method of generating a yield map for a baler according to the twenty-third aspect, the computer program according to the thirty-fifth aspect, and the computer readable storage medium according to the forty-seventh aspect, it is possible to generate a yield map in which the yields are correlated with the positions, respectively.

With the yield map generation system according to the twelfth aspect, the method of generating a yield map for a baler according to the twenty-fourth aspect, the computer program according to the thirty-sixth aspect, and the computer readable storage medium according to the forty-eighth aspect, it is possible to generate a yield map in which the yield level is shown in each of the regions of the field.

The present application refers to words "include" and derivatives as nonrestrictive terms for description of provision of constituent elements, without exclusion of any other constituent element not referred to in the present application. The same applies to words "have", "provided with", and derivatives thereof.

Expressions "member", "part", "element", "body", and "structure" may have a plurality of meanings indicating a single portion and a plurality of portions.

Ordinal numbers "first", "second", and the like are terms for simple distinction among configurations, without having any other meaning (e.g. specific order). For example, provision of a "first element" does not indicate provision of a "second element", and provision of the "second element" does not indicate provision of the "first element".

Expressions "substantially", "approximately", "about", and the like indicating degrees may each have a rational deviation not significantly changing a final result. All the numerical values referred to in the present application may be interpreted as including any one of the expressions "substantially", "approximately", "about", and the like.

In the present application, an expression "at least one of A and B" is interpreted to encompass (1) only A, (2) only B, and (3) both A and B.

In view of the above disclosure, the present invention can obviously include various modifications and alterations. The present invention may thus be implemented in any manner different from those specifically disclosed in the present application without departing from the spirit of the preset invention.

What is claimed is:

1. A yield calculation system comprising:
a position sensor configured to detect a position;
a baler configured to form crop material into bales and comprising:
  a bale chamber in which the crop material is to be formed into each of the bales;
  a volume measurement sensor provided in the bale chamber and configured to measure a volume of each of the bales in the bale chamber, the volume corresponding to the position detected by the position sensor;
  a moisture measurement sensor provided in the bale chamber and configured to measure a moisture weight ratio of a portion of each of the bales, the moisture weight ratio indicating a ratio of a moisture weight of the portion of each of the bales to a weight of the portion of each of the bales, the moisture weight ratio corresponding to the position detected by the position sensor; and
  a weight measurement sensor configured to measure a reference bale weight indicating a weight of a reference volume of each of the bales, when the volume of each of the bales amounts to the reference volume, the reference volume being a volume of a completed bale that is formed just before being discharged from the bale chamber;
a memory configured to store a reference unit volume weight indicating a unit volume weight of a remainder in which moisture is excluded from the crop material; and
circuitry configured to
  calculate an original value of the reference unit volume weight stored in the memory based on the reference bale weight of a previous bale of the bales, the reference volume of the previous bale, and the moisture weight ratios of the previous bale which are measured in a time taken for the previous bale to be formed into the completed bale,
  obtain an increment of the volume of a target bale of the bales in a predetermined cycle, the target bale being formed subsequent to the previous bale,
  obtain the moisture weight ratio corresponding to the increment of the volume of the target bale,
  calculate, based on the original value of the reference unit volume weight stored in the memory, the increment of the volume of the target bale, and the moisture weight ratio corresponding to the increment, a yield in the predetermined cycle, the yield indicating a remaining weight obtained by excluding a moisture weight of the increment from a weight of the increment, and
  change the reference unit volume weight stored in the memory from the original value to an updated value based on the reference bale weight of the target bale, the reference volume of the target bale, and the moisture weight ratios of the target bale which are measured in a time taken for the target bale to be formed into the completed bale.

2. The yield calculation system according to claim 1, wherein the volume measurement sensor is configured to measure a diameter of each of the bales.

3. The yield calculation system according to claim 1, further comprising:
a tractor configured to move the baler,
wherein the position sensor is provided on at least one of the baler and the tractor.

4. The yield calculation system according to claim 1, wherein the predetermined cycle is constituted by at least one of a predetermined time and an amount of change of the position.

5. The yield calculation system according to claim 1, wherein the circuitry is configured to
  calculate an average moisture weight ratio of the previous bale based on the moisture weight ratios of the previous bale,
  calculate an average moisture weight ratio of the target bale based on the moisture weight ratios of the target bale,
  calculate the original value of the reference unit volume weight based on the reference bale weight of the previous bale, the reference volume of the previous bale, and the average moisture weight ratio of the previous bale, and
  change the reference unit volume weight to the updated value based on the reference bale weight of the target bale, the reference volume of the target bale, and the average moisture weight ratio of the target bale.

6. The yield calculation system according to claim 5, wherein the circuitry is configured to
  obtain a reference moisture weight indicating a moisture weight in the reference volume of the target bale by multiplying the reference bale weight of the target bale by the average moisture weight ratio of the target bale,
  obtain a moisture volume in the reference volume of the target bale by dividing the reference moisture weight of the target bale by a unit volume weight of water, obtain a remaining bale weight in the reference volume of the target bale by subtracting the reference moisture weight from the reference bale weight of the target bale, obtain a remaining bale volume in the reference volume of the target bale by subtracting the moisture volume from the reference volume of the target bale, obtain a bale remainder unit volume weight by dividing the remaining bale weight by the remaining bale volume, and weighted average the original value of the reference unit volume weight and the bale remainder unit volume weight to obtain the updated value of the reference unit volume weight.

7. The yield calculation system according to claim 1, wherein the circuitry is configured to calculate the yield using the following equation:

$$Gi = \rho_R \times V_i / \{1 + M_i \times 10^{-2} \times (\rho_R/\rho_W - 1)\},$$

where:
$\rho_R$ is the original value of the reference unit volume weight [kg/m$^3$];
$\rho_W$ is a unit volume weight of water [kg/m$^3$];
$V_i$ is an i-th increment of the volume of the bale, the i-th increment being the increment in an i-th cycle [m$^3$] (i is an integer);
$M_i$ is a percentage of the moisture weight ratio in the i-th increment [wt %] ($M_i$ corresponds to $V_i$); and
$G_i$ is an i-th yield [kg] ($G_i$ corresponds to $V_i$).

8. A yield map generation system comprising:
the yield calculation system according to claim 1,
wherein the circuitry is configured to generate a yield map in which the yield is correlated with the position detected in the predetermined cycle.

9. A yield map generation system comprising:
the yield calculation system according to claim 1,
wherein the circuitry is configured to
determine an area of a field,
divide the area into regions based on a raked track in the area, the baler being configured to travel along the raked track to form the bale,
determine region yields in the regions, respectively, by correlating, with one of the regions, the yield calculated in the predetermined cycle,
divide region yields by dimensions of the regions to obtain unit yields in the regions, respectively, and
generate a yield map in which the regions are correlated with yield levels calculated based on the unit yields, respectively.

10. A method of calculating a yield for a baler, comprising:
obtaining a position at which the baler harvests crop material;
obtaining a volume of each of bales into which the crop material is formed in a bale chamber of the baler; the volume of each of the bales corresponding to the position;
obtaining a moisture weight ratio of a portion of each of the bales, the moisture weight ratio indicating a ratio of a moisture weight of the portion of each of the bales to a weight of the portion of each of the bales, the moisture weight ratio corresponding to the position;
measuring a reference bale weight indicating a weight of a reference volume of each of the bales, when the volume of each of the bales amounts to the reference volume, the reference volume being a volume of a completed bale that is formed just before being discharged from the bale chamber;
calculating an original value of a reference unit volume weight indicating a unit volume weight of a remainder in which moisture is excluded from the crop material based on the reference bale weight of a previous bale of the bales, the reference volume of the previous bale, and the moisture weight ratios of the previous bale which are measured in a time taken for the previous bale to be formed into the completed bale;
obtaining an increment of the volume of a target bale of the bales in a predetermined cycle, the target bale being formed subsequent to the previous bale;
obtaining the moisture weight ratio corresponding to the increment of the volume of the target bale;
calculating, based on the original value of the reference unit volume weight, the increment of the volume of the target bale, and the moisture weight ratio corresponding to the increment, the yield in the predetermined cycle, the yield indicating a remaining weight obtained by excluding a moisture weight of the increment from a weight of the increment; and
changing the reference unit volume weight from the original value to an updated value based on the reference bale weight of the target bale, the reference volume of the target bale, and the moisture weight ratios of the target bale which are measured in a time taken for the target bale to be formed into the completed bale.

11. The method according to claim 10, wherein the volume of each of the bales is obtained by measuring a diameter of each of the bales.

12. The method according to claim 10, wherein the position is obtained by a position sensor provided on at least one of the baler and a tractor configured to move the baler.

13. The method according to claim 10, wherein the predetermined cycle is constituted by at least one of a predetermined time and an amount of change of the position.

14. A non-transitory computer-readable storage medium storing a program for causing a computer to perform a method of calculating a yield for a baler, the method comprising:
obtaining a position at which the baler harvests crop material;
obtaining a volume of each of bales into which the crop material is formed in a bale chamber of the baler, the volume of each of the bales corresponding to the position;
obtaining a moisture weight ratio of a portion of each of the bales, the moisture weight ratio indicating a ratio of a moisture weight of the portion of each of the bales to a weight of the portion of each of the bales, the moisture weight ratio corresponding to the position;
obtaining a reference bale weight indicating a weight of a reference volume of each of the bales, when the volume of each of the bales amounts to the reference volume, the reference volume being a volume of a completed bale that is formed just before being discharged from the bale chamber;
calculating an original value of a reference unit volume weight indicating a unit volume weight of a remainder in which moisture is excluded from the crop material based on the reference bale weight of a previous bale of the bales, the reference volume of the previous bale, and the moisture weight ratios of the previous bale which are measured in a time taken for the previous bale to be formed into the completed bale;

obtaining an increment of the volume of a target bale of the bales in a predetermined cycle, the target bale being formed subsequent to the previous bale;

obtaining the moisture weight ratio corresponding to the increment of the volume of the target bale;

calculating, based on the original value of the reference unit volume weight, the increment of the volume of the target bale, and the moisture weight ratio corresponding to the increment, the yield in the predetermined cycle, the yield indicating a remaining weight obtained by excluding a moisture weight of the increment from a weight of the increment; and changing the reference unit volume weight from the original value to an updated value based on the reference bale weight of the target bale, the reference volume of the target bale, and the moisture weight ratios of the target bale which are obtained in a time taken for the target bale to be formed into the completed bale.

15. The yield calculation system according to claim 1, wherein the circuitry is configured to obtain the increment of the volume of the target bale while the target bale is being formed in the bale chamber, obtain the moisture weight ratio corresponding to the increment of the volume of the target bale while the target bale is being formed in the bale chamber, and calculate the yield in the predetermined cycle while the target bale is being formed in the bale chamber.

16. The method according to claim 10, wherein the increment of the volume of the target bale is obtained while the target bale is being formed in the bale chamber, wherein the moisture weight ratio corresponding to the increment of the volume of the target bale is obtained while the target bale is being formed in the bale chamber, and wherein the yield in the predetermined cycle is calculated while the target bale is being formed in the bale chamber.

17. The non-transitory computer-readable storage medium according to claim 14, wherein the increment of the volume of the target bale is obtained while the target bale is being formed in the bale chamber, wherein the moisture weight ratio corresponding to the increment of the volume of the target bale is obtained while the target bale is being formed in the bale chamber, and wherein the yield in the predetermined cycle is calculated while the target bale is being formed in the bale chamber.

* * * * *